(12) United States Patent
Ouzounov et al.

(10) Patent No.: US 11,112,594 B2
(45) Date of Patent: Sep. 7, 2021

(54) DUAL MODE MICROENDOSCOPE CONCENTRATING LIGHT EMISSION INTO RING AREA

(71) Applicant: CORNELL UNIVERSITY, Ithaca, NY (US)

(72) Inventors: Dimitre G Ouzounov, Ithaca, NY (US); Chunhui (Chris) Xu, Ithaca, NY (US); Watt W. Webb, Ithaca, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 539 days.

(21) Appl. No.: 14/400,257

(22) PCT Filed: May 10, 2013

(86) PCT No.: PCT/US2013/040547
§ 371 (c)(1),
(2) Date: Nov. 10, 2014

(87) PCT Pub. No.: WO2013/170145
PCT Pub. Date: Nov. 14, 2013

(65) Prior Publication Data
US 2015/0131147 A1     May 14, 2015

Related U.S. Application Data

(60) Provisional application No. 61/645,581, filed on May 10, 2012.

(51) Int. Cl.
*G02B 17/08* (2006.01)
*G02B 21/06* (2006.01)
(Continued)

(52) U.S. Cl.
CPC ...... *G02B 23/2438* (2013.01); *A61B 1/00096* (2013.01); *A61B 1/00188* (2013.01);
(Continued)

(58) Field of Classification Search
CPC ............ A61B 1/00096; A61B 1/00165; A61B 1/00167; A61B 1/0017; A61B 1/00188;
(Continued)

(56) References Cited

U.S. PATENT DOCUMENTS 5,555,131 A * 9/1996 Horton ...................... G02B 1/02
359/661
5,568,312 A * 10/1996 Horton ................... G02B 13/18
359/362

(Continued)

FOREIGN PATENT DOCUMENTS

| CN | 101909509 A | 12/2010 |
| JP | 2012037768 A | 2/2012 |
| WO | 2009002467 A2 | 12/2008 |

OTHER PUBLICATIONS

PCT International Search Report and Written Opinion, International Application No. PCT/US2013/040547, pp. 1-12, International Filing Date: May 10, 2013.

*Primary Examiner* — Ryan S Dunning
(74) *Attorney, Agent, or Firm* — Bond Schoeneck & King, PLLC; Blaine T. Bettinger

(57) ABSTRACT

A microendoscope, and a microendoscopy method related to the microendoscope, each include a tube housing, where an end of the tube housing is shaped and finished to facilitate collection of light emitted from a sample when examined using the microendoscope. In addition, a catadioptric lens assembly, an endomicroscope that includes the catadioptric lens assembly and a microendoscopy method for microscopic analysis that uses the endomicroscope are predicated upon a second element and a third element within the catadioptric lens assembly that each has a dichroic coating. The placement of the dichroic coating on the second element (Continued)

and the third element provides for different magnification factors as a function of illumination wavelength when using the microendoscopy method.

15 Claims, 5 Drawing Sheets

(51) Int. Cl.
 G02B 21/16 (2006.01)
 G02B 23/24 (2006.01)
 A61B 1/00 (2006.01)
 A61B 1/06 (2006.01)
 A61B 1/04 (2006.01)

(52) U.S. Cl.
 CPC ............ *A61B 1/043* (2013.01); *A61B 1/0638* (2013.01); *G02B 17/0896* (2013.01); *G02B 21/06* (2013.01); *G02B 21/16* (2013.01)

(58) Field of Classification Search
 CPC ... A61B 1/0638; A61B 1/043; A61B 1/00066; A61B 1/00071; A61B 1/00117; A61B 1/00163; A61B 1/00174; A61B 1/00181; G02B 17/0896; G02B 21/06; G02B 21/16; G02B 23/2423; G02B 23/243; G02B 23/2438; G02B 23/2461; G02B 23/2469; G02B 23/2476; G02B 23/26; G02B 23/2407; G02B 23/2446; G02B 23/2453

USPC ....... 359/364, 368, 385, 513, 514, 726, 727; 362/572, 574, 575; 385/116–121; 600/101, 160, 170, 171, 176, 177, 182

See application file for complete search history.

(56) References Cited

U.S. PATENT DOCUMENTS

| | | | |
|---|---|---|---|
| 5,587,839 A * | 12/1996 | Miyano | G02B 9/34 |
| | | | 359/660 |
| 5,662,584 A * | 9/1997 | Hori | A61B 1/00096 |
| | | | 348/65 |
| 6,006,001 A | 12/1999 | Alfano et al. | |
| 6,639,203 B1 | 10/2003 | Kerschner | |
| 2002/0041445 A1 | 4/2002 | Nishioka et al. | |
| 2003/0179448 A1* | 9/2003 | Ramsbottom | G02B 23/26 |
| | | | 359/435 |
| 2003/0214726 A1* | 11/2003 | Mihara | G02B 15/177 |
| | | | 359/676 |
| 2007/0293874 A1* | 12/2007 | Okada | A61B 17/320016 |
| | | | 606/113 |
| 2008/0051632 A1* | 2/2008 | Ito | A61B 1/0607 |
| | | | 600/114 |
| 2008/0080060 A1 | 4/2008 | Messerschmidt | |
| 2009/0062658 A1* | 3/2009 | Dunki-Jacobs | A61B 1/00096 |
| | | | 600/476 |
| 2010/0026456 A1* | 2/2010 | Cline | A61B 1/00059 |
| | | | 340/10.1 |
| 2010/0204609 A1 | 8/2010 | Worth et al. | |
| 2010/0261958 A1 | 10/2010 | Webb et al. | |
| 2011/0125029 A1 | 5/2011 | Wang et al. | |
| 2011/0157596 A1* | 6/2011 | Wax | G01B 9/02091 |
| | | | 356/456 |
| 2011/0196200 A1 | 8/2011 | Glozman et al. | |

* cited by examiner

| Parameters | High-Magnification Mode | Low-magnification mode |
|---|---|---|
| Sample space | Water | air |
| Magnification | -0.2X | -1.47X |
| NA | 0.55 | 0.082 |
| FOV | 180 um | 1.3 mm |
| Linear Resolution | 0.7 um | 4.5 um |
| Wavelength | 800-950 nm | 350-750 nm |
| Working distance | 140 um | 3 mm |
| Axial resolution | 10.5 um | NA |

Experimental set-up

DUAL MODE MICROENDOSCOPE CONCENTRATING LIGHT EMISSION INTO RING AREA

CROSS-REFERENCE TO RELATED APPLICATION

This application is a U.S. National Phase filing of International Application No. PCT/US2013/040547 filed May 10, 2013, which itself claims priority from U.S. Provisional Patent Application Ser. No. 61/645,581, filed 10 May 2012 and titled Dual Mode Microendoscope, the subject matter of which are each incorporated herein fully by reference in their entirety.

GOVERNMENT FUNDING

This invention was made with government support under grant number EB006736 and CA133148 awarded by the National Institutes of Health. The government has certain rights in the invention.

BACKGROUND

1. Field of the Invention

Embodiments relate generally to microendoscope apparatus, methods and applications. More particularly, embodiments relate to dual mode microendoscope apparatus, methods and applications.

2. Description of Related Art

A number of optical imaging modalities have been used for endoscopic imaging, potentially providing real-time tissue diagnostics in a clinical setting. In that regard, optical zoom capability is an essential requirement for a practical endoscope because high spatial resolution and large field-of-view (FOV) cannot be achieved simultaneously by one miniature objective lens. In a clinical environment, a low-resolution/large FOV would allow a clinician to survey a large area to identify sites of interest. By switching to a high-resolution/small FOV, a clinician would be able to resolve cellular details at the sites of interest. For practical implementation, both large FOV imaging and high-resolution imaging must be obtained with the same endoscope apparatus.

While optical zoom capability is easily implemented in a conventional microscope by switching among multiple objective lenses, this mechanical approach is impractical to implement in a miniature endoscope due to size limitations. Thus, desirable are miniature endoscope apparatus, related methods and related applications that possess a facile zoom capability.

SUMMARY

Embodiments provide a dual modality microendoscope with a miniature optical zoom lens that requires no mechanical adjustment of the distal elements. The multiphoton modality provides high-magnification/resolution, small FOV imaging, and the one-photon reflectance modality provides low-magnification/resolution, large FOV imaging. The two imaging modes are switched by changing the wavelength of the excitation light.

Embodiments also provide a microendoscope wherein an end of a tube housing that houses a lens assembly within the microendoscope is shaped and finished to facilitate collection of light emitted from a sample when examined while using the microendoscope.

A particular microendoscope in accordance with the embodiments includes a tube housing that defines an optical path. This particular microscope also includes a lens assembly positioned within an end of the tube housing to couple with a sample external to the tube housing, where the end of the tube housing is shaped and finished to facilitate collection of light emitted from the sample when examined using the microendoscope.

A particular microendoscopy method in accordance with the embodiments includes providing a microendoscope comprising: (1) a tube housing that defines an optical path; and (2) a lens assembly positioned within an end of the tube housing to couple with a sample external to the tube housing, where the end of the tube housing is shaped and finished to facilitate collection of light emitted from the sample when examined using the microendoscope. This particular microendoscopy method also includes examining the sample while using the microendoscope.

A particular catadioptric lens assembly in accordance with the embodiments includes a second element including a convex proximal surface and a concave distal surface. This particular catadioptric lens assembly also includes a third element including a convex proximal surface coupled with the concave distal surface of the second element, as well as a flat distal surface, at least a portion of each of the second element and the third element including a dichroic coating.

Another particular microendoscope in accordance with the embodiments includes within an optical path a second element including a convex proximal surface and a concave distal surface. The particular microendoscope also includes a third element including a convex proximal surface coupled with the concave distal surface of the second element, as well as a flat distal surface, at least a portion of each of the second element and the third element including a dichroic coating.

Another particular microendoscopy method in accordance with the embodiments includes providing a microendoscope comprising within an optical path: (1) a second element including a convex proximal surface and a concave distal surface; and (2) a third element including a convex proximal surface coupled with the concave distal surface of the second element, as well as a flat distal surface, at least a portion of each of the second element and the third element including a dichroic coating. This particular microendoscopy method also includes coupling the microendoscope to a sample. This particular microendoscopy method also includes securing a first endoscopy image of the sample at a first magnification while using a first irradiation wavelength. This particular microendoscopy method also includes securing a second endoscopy image of the sample at a second magnification different than the first magnification while using a second irradiation wavelength different than the first irradiation wavelength.

As used herein, the terms 'emission' and 'light emission' refer to single- and multi-photon fluorescence generated light, scattered light, reflected light, and higher-order-generated light, as a person skilled in the art would understand.

BRIEF DESCRIPTION OF THE DRAWINGS

The objects, features and advantages of the embodiments are understood within the context of the Detailed Description of the Embodiments, as set forth below. The Detailed Description of the Embodiments is understood within the context of the accompanying drawings, that form a material part of this disclosure, wherein.

DETAILED DESCRIPTION OF THE EMBODIMENTS

Embodiments provide a dual modality microendoscope with a miniature optical zoom lens chat requires no mechanical adjustment of the distal elements. The multiphoton modality provides high-magnification/resolution, small FOV imaging, and the one-photon reflectance modality provides low-magnification/resolution, large FOV imaging. The two imaging modes are switched by changing the wavelength of the excitation light.

An element of the endoscope is a catadioptric zoom lens (FIG. 1a) based on the idea of separating the optical paths of excitation light with different wavelengths. Starting from the left in FIG. 1a, light emerging from the delivery/scanning optical fiber is directed by element #1 onto the multilayered, patterned dichroic coating deposited at the center of the proximal surface of element #3. Depending on the incident wavelength, the excitation light is either: (1) reflected (e.g., i=800 nm) to the dichroic coating on the proximal surface of element #2 (FIG. 1b) and then focused to the sample with high numerical aperture (NA), or: (2) transmitted (e.g., i=406 nm) and focused to the sample with low NA. Therefore, the optical zoom operation is achieved by changing the wavelength of the excitation light without any mechanical adjustment.

Figure 1:
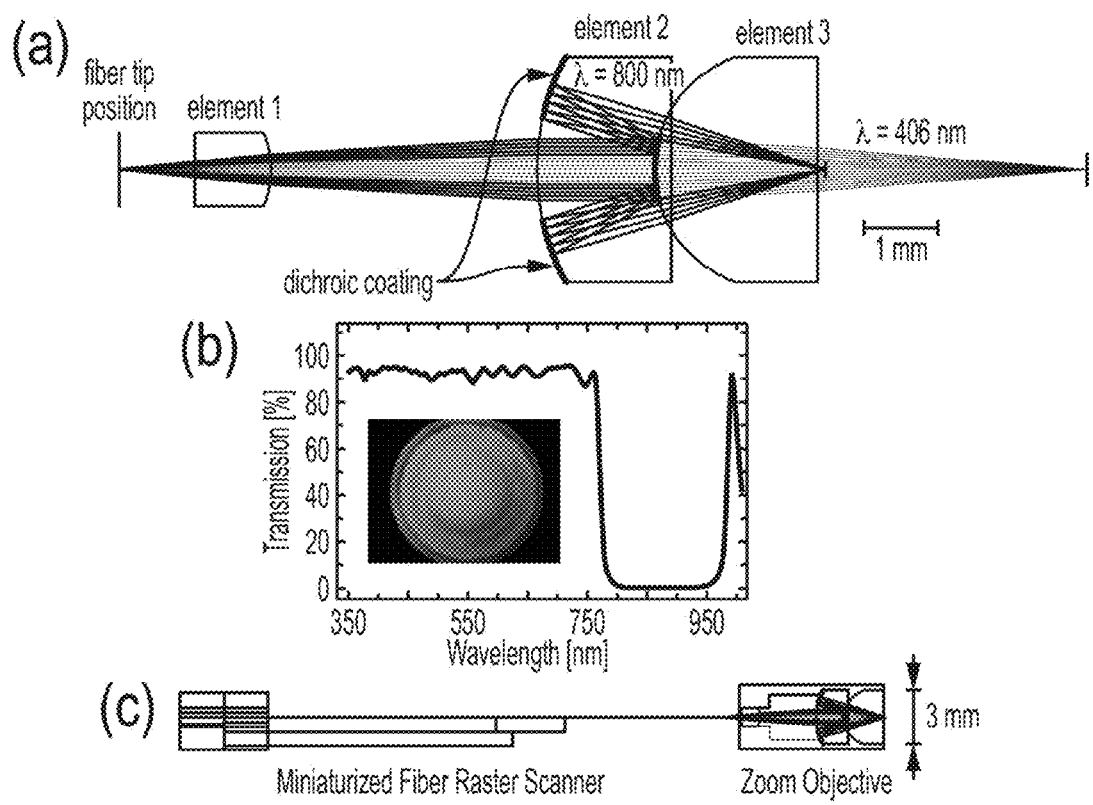
FIG. 1 shows: (a) Zoom microendoscope objective design layout, drawn to scale, (b) Transmission curve of the patterned dichroic coating deposited on the proximal surface of element #2 (shown in the inset). The coating at the center of the proximal surface of element #3 has similar spectral curve, (c) Alignment diagram of the fiber scanner and the zoom lens.

In accordance with the embodiments, one may pair an (illuminated) zoom lens in free space with a conventional miniaturized resonant/non-resonant fiber raster scanner (FIG. 1c). The scanner incorporates two scanning optical fibers glued together: (1) a hollow-core photonic band-gap fiber (HC-PBGF, HC-800-2, NKT Photonics) with a transmission window at 800 nm for high-resolution multiphoton imaging; and (2) a standard single mode fiber (SSMF) at 400 nm for large FOV, one-photon imaging.

For high-resolution multiphoton imaging, one may couple femtosecond pulses centered at 800 nm into the HC-PBGF. To compensate for the anomalous dispersion of the HC-PBGF, the pulses were pre-chirped by passing through a piece of SF 11 glass. The output pulse width from the PBGF was measured to be 90 fs. A fiber coupled CW laser diode (LP406-SF20, Thorlabs) operating at 406 nm was coupled into the SSMF for large FOV, one-photon reflectance imaging. One may choose 406 nm for one-photon reflectance imaging since it is one of the preferred excitation wavelengths for narrow-band imaging.

Figure 2:
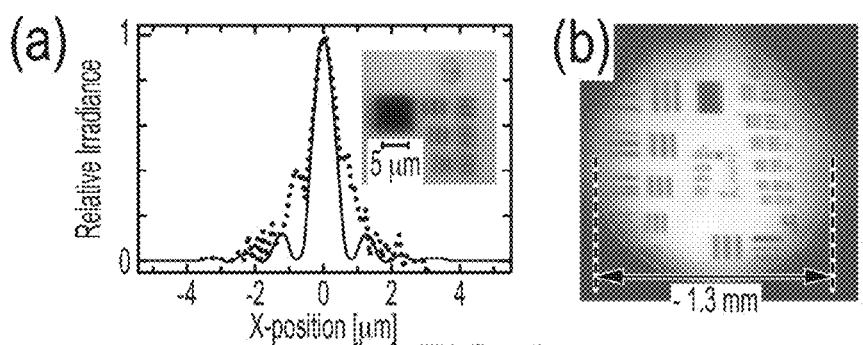
FIG. 2 shows: (a) Calculated (solid line) and measured (dashed line) lateral point spread function for the high-resolution imaging mode. Inset: Group 9 of USAF high-resolution target imaged in transmission using the high-resolution imaging, (b) USAF resolution target imaged in transmission using the low-magnification mode (i=406 nm)

One may test the performance of the dual zoom microendoscope by imaging a US Air Force (USAF) test target in transmission. The lateral resolution of the high-magnification mode (FWHM) is ~0.8 um (FIG. 2a), which corresponds to a two-photon resolution of 0.57 um. The FOV of the high-magnification mode is 150 mm. Note that high-resolution and near diffraction-limited performance are achieved with only 3 optical elements. The one-photon lateral resolution of the low magnification mode was also measured to be ~4.5 um. The low-magnification mode achieved an extraordinarily large FOV of 1.3 mm (FIG. 2b) for a 3 mm OD lens. One may further characterize the two-photon axial resolution of the high-magnification mode by stepping a 500-nm Rhodamine B thin film through the high-magnification focal spot. The measured FWHM of the thin film response is ~11 um.

Figure 3:
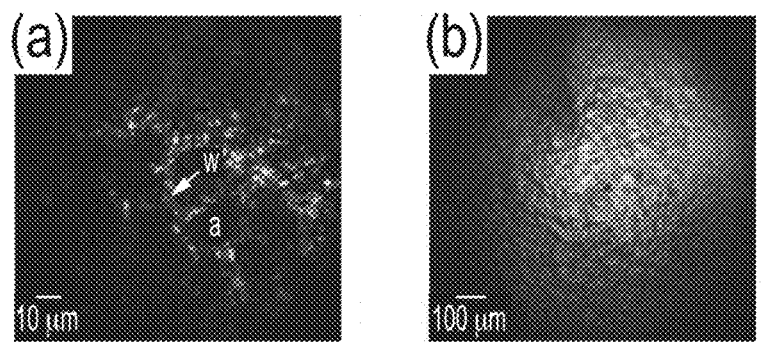
FIG. 3 shows: (a) Two-photon intrinsic fluorescence/scattering image of unstained ex vivo mouse lung tissue in high-resolution mode, (b) Reflection/Scattering image of unstained ex vivo mouse lung in low-resolution mode.

To demonstrate the capability of the dual modality, dual optical zoom microendoscope one may image unstained ex vivo mouse lung tissue. Prior to imaging, a normal deflated lung lobe was cut to allow for direct inspection of the interior of the lung. The dichroic coatings on elements 2 and 3 (FIG. 1a) that enable zoom operation make it impossible to use the delivery fiber for epi-collection of the two-photon excited fluorescence or scattered signal. Therefore, one may use 10 plastic optical fibers with large core diameter (500 um) located just behind element 2 to collect the fluorescence or scattered signal (see, e.g., Additional Embodiments), FIG. 3a shows a high-resolution two-photon image of unstained mouse lung. The image was acquired using 60 mW average power at the sample (5 frames averaged). Characteristic lung features including alveolar lumens (a) and walls (w) are clearly distinguishable. FIG. 3b shows a low-magnification reflection/scattering image of mouse lung. Here, the hollow circular alveoli are visible. All images were acquired at 2 frames/s.

In conclusion, designed, built and characterized herein is a microendoscope objective that provides optical zoom capability without any mechanical adjustment of the distal elements. One may demonstrate the function of the objective lens for endoscopic imaging by pairing it with a miniature fiber raster scanner. Imaged herein was unstained ex vivo mouse lung tissues using both high-resolution multiphoton and low-magnification reflectance imaging modes. Such a dual modality, dual optical zoom microendoscope represents an important step forward in bringing multiphoton imaging to the clinic.

Microendoscope Tube Housing Considerations

Figure 8:
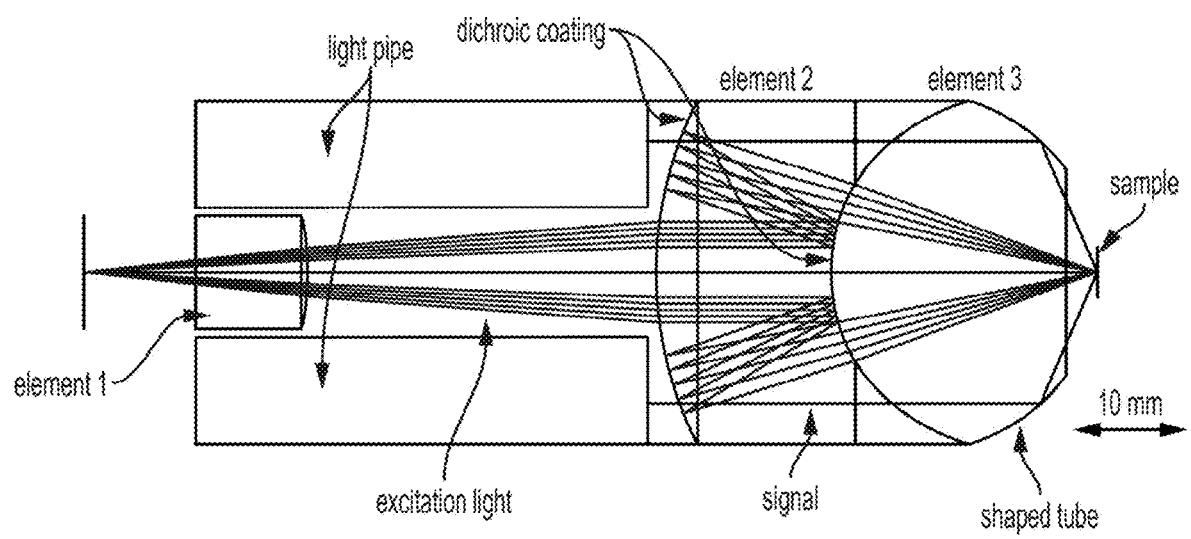
FIG. 8 shows a schematic diagram of a catadioptric lens assembly in accordance with the embodiments located within a tube housing within the context of a microendoscope apparatus.

FIG. 8 shows a schematic diagram of a catadioptric lens assembly in accordance with the embodiments located within a microendoscope tube housing to provide a microendoscope in accordance with the embodiments. Notable within FIG. 8 is that the tube housing (i.e., shaped-tube) is shaped and finished to facilitate collection of fluorescent or scattered emitted light radiation from a sample that is examined while using a microendoscope in accordance with the embodiments.

To provide such enhanced emitted light collection, the end of the shaped tube may have any of several particular shapes, such as but not limited to a parabola and a sphere. As well, the interior surface of the end of the tube housing is coated with a highly reflective material, such as but not limited to silver, gold, aluminum, and other highly reflective coating materials known in the art. The tube/housing may extend proximally a distance from about 4 millimeters to about 8 millimeters from element 2 component as illustrated in FIG. 8.

Figure 4:
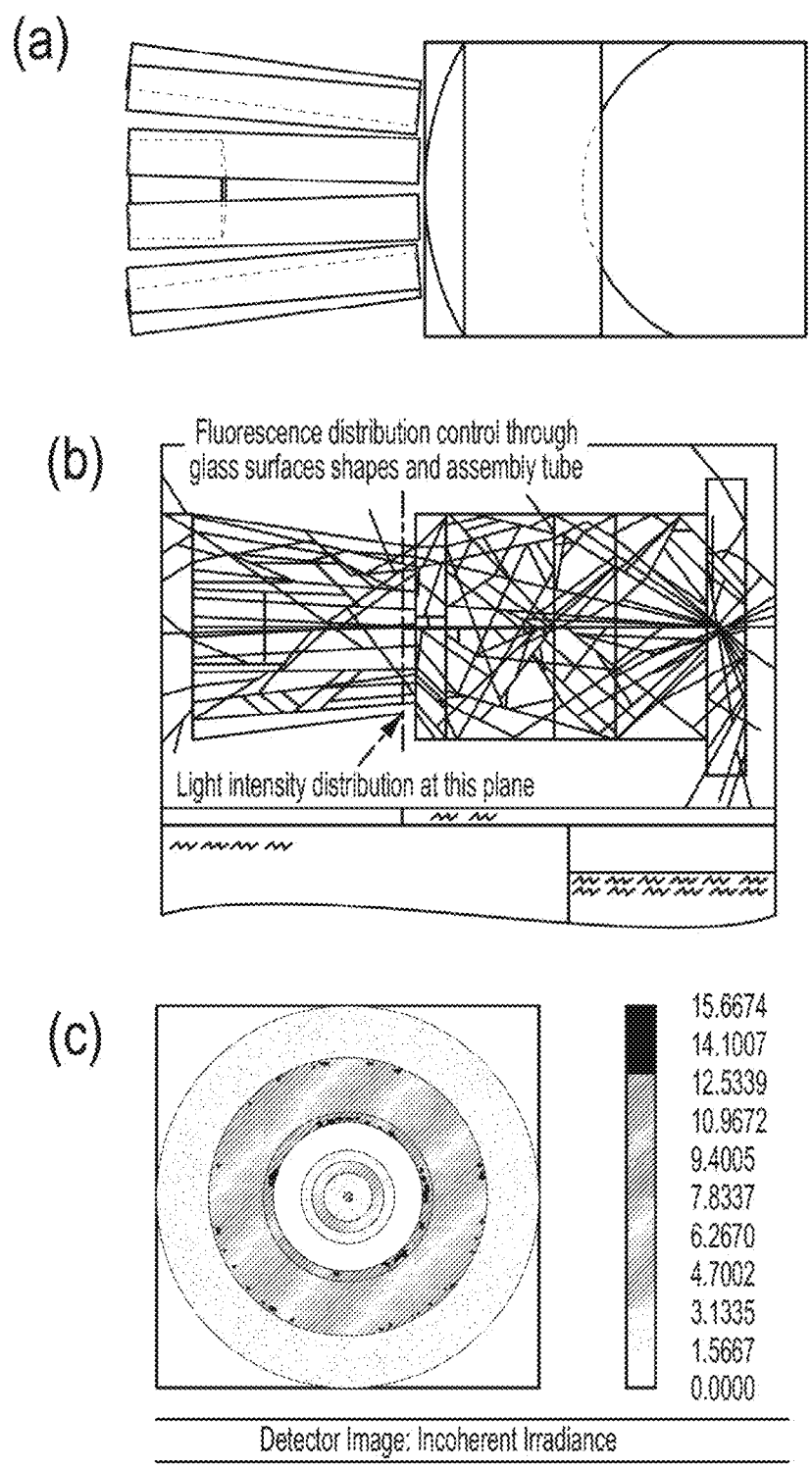
FIG. 4 shows: (a) 3D schematic of catadioptric objective with light pipes as light emission collectors, (b) The emission signal propagation is shaped by the assembly tube and optics, (c) Emission distribution at the plane immediately before element 3.

A schematic diagram of a microendoscope is shown in FIG. 4, The microendoscope uses light pipes as a light collection component. Even without special shaping of the tube (i.e., simply assuming mirror finish on the inner tube surface), the distribution of the back-propagating light could be effectively controlled by the tube and the optical elements. For example, the emitted light distribution in the plane (dashed line in FIG. 4b) at the front of element #2 is about 55% (FIG. 4c) of the total emitted light. With most of the emitted light concentrated within a ring area, it is feasible to collect most of the light with suitably placed light pipes. The numerical simulation shows that a single acrylate light pipe with a core diameter of 500 microns, placed to overlap with the maximum of the emission distribution, collects ~2% of the emitted light. Ten light pipes would collect ~20%, which is comparable to the ideal case for excitation fiber collection with an objective lens of NA=0.8. By designing the light pipes to cover the ring area more completely, more emitted light can be collected (up to 40% more). The design in accordance with these additional embodiments represents a significant improvement over all existing endoscope collection optics, and it will greatly improve the applicability of multiphoton endoscopes. The device has demonstrated good light collection efficiency and produced high-quality MPM images.

The new collection scheme in accordance with the additional embodiments has the potential to provide useful information beyond the emitted light. Each light pipe looks at the excitation volume at a different angle; and detecting the signal from each pipe separately, one may derive information about the directional distribution of the emitted light due to sample structure and morphology.

Figure 5:
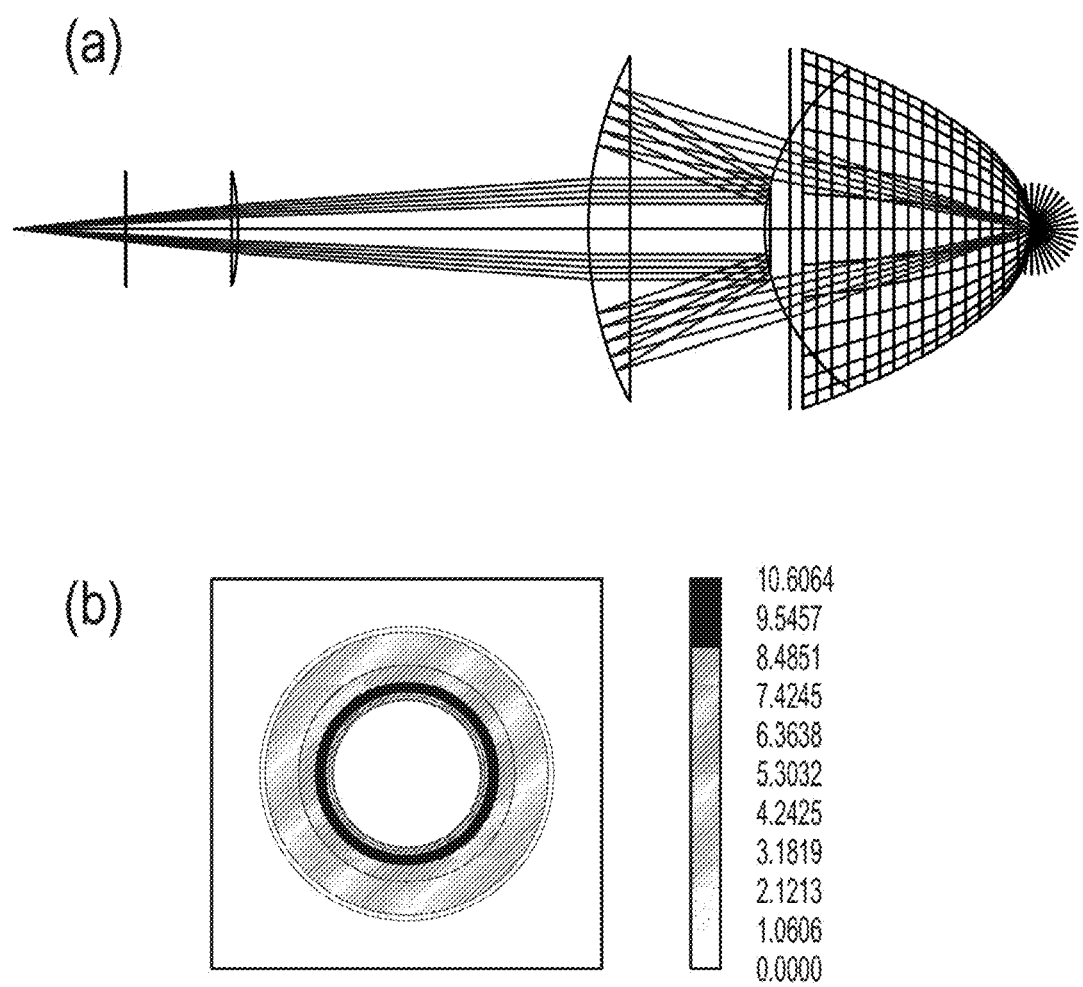
FIG. 5 shows: (a) Shaped end of the assembly tube directs the distribution of the emitted light in a ring area, (b) Emitted light distribution in the plane immediately before the second lens.

As illustrated in FIG. 5, the distal end of the assembly tube/housing is shaped in a form that is optimized to direct the emission mostly into a ring area (FIG. 5b). Using the tube shape as a design parameter, the collection efficiency may be comparatively high.

Any of the above embodiments is accompanied with light pipes that could be specifically designed to fit the space and placed to interface the area where emitted light distribution is maximal.

Figures 6, 7:
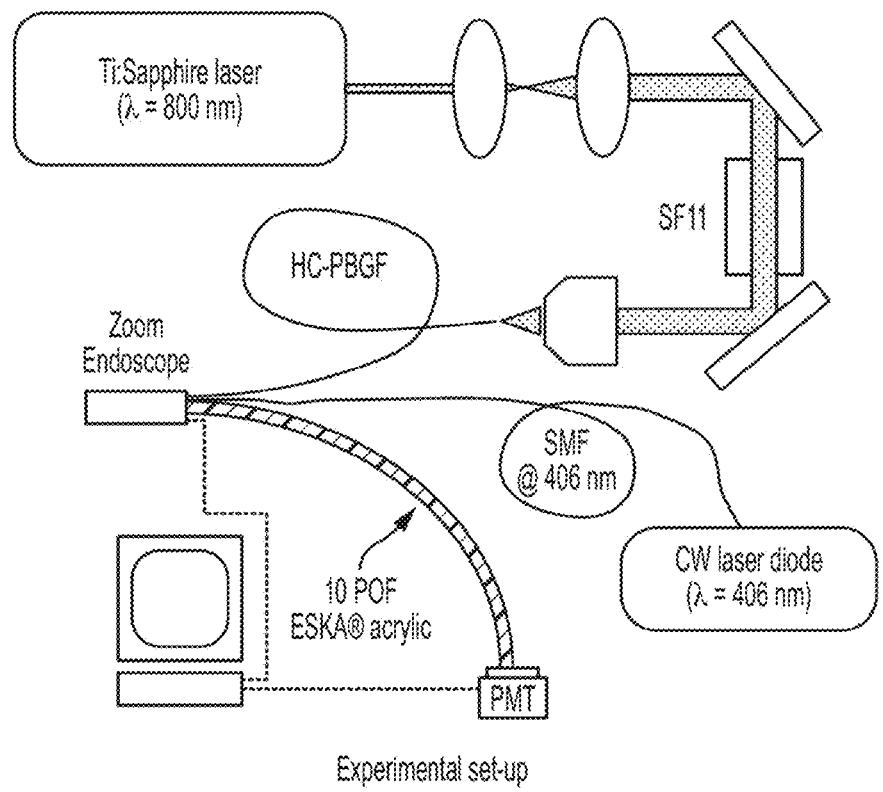
FIG. 6 shows a table including design specifications for a non-limiting exemplary catadioptric lens assembly and a related microendoscope in accordance with the embodiments.
FIG. 7 shows a schematic diagram illustrating an assemblage of apparatus that may be used for providing a microendoscope in accordance with the embodiments.

FIG. 6 shows a table including design specifications for a non-limiting exemplary catadioptric lens assembly and a related microendoscope in accordance with the embodiments, to allow a person of ordinary skill in the art to practice the embodiments.

FIG. 7 shows a schematic diagram illustrating an assemblage of apparatus that may be used for providing a microendoscope in accordance with the embodiments.

Miniature Zoom Lens Design and Fabrication

As noted above, within the embodiments, the optical zoom operation is provided by a miniature, three-element catadioptric lens that separates the optical paths of excitation light with different wavelengths. The miniature objective lens may have a 3 mm outside diameter (OD) and is ~8 mm in length. The zoom function is enabled by the dichroic coatings deposited at the central part of the proximal surface of element #3 and at the peripheral region of the proximal surface of element #2. The central part of the proximal surface of element #2 is uncoated. Starting from the left in FIG. 1a, the excitation light emerges from the delivery/scanning fiber and is directed by element #1 onto the dichroic coating at the central part of the proximal surface of element #3. Depending on the incident wavelength ($\lambda_i$), the excitation light is either reflected (e.g., for $\lambda_i$=800 nm) to the patterned dichroic coating on the proximal surface of element #2 and then focused to the sample with high numerical aperture (NA), or transmitted (e.g., for $\lambda_i$=406 nm) and focused to the sample with low NA. Therefore, the optical zoom operation is achieved by changing the wavelength of the excitation light without any mechanical adjustment.

The high-resolution multiphoton imaging mode is designed to operate between 800 to 950 nm. At $\lambda_i$=800 nm, the calculated full width at half maximum (FWHM) of the lateral point spread function (PSF) is 0.7 um, and the Strehl ratio is approximately 1 over the central 150-um FOV, indicating diffraction limited optical performance. The low-magnification imaging mode operates between 350 to 750 nm. At $\lambda_i$=406 nm, the lateral resolution (FWHM) is 4.5 um, and the FOV is 1.3 mm. The simulated Strehl ratio is 0.82, which is greater than the value (0.8) accepted for a system well corrected for aberrations. 406 nm was chosen for one-photon reflectance imaging since it is one of the preferred excitation wavelengths for narrow-band imaging. In both imaging modes, the focal planes of the miniature zoom lens have small curvatures. Such a curved image plane allows significantly better aberration correction than a planar image plane, and is inconsequential for in vivo tissue imaging. Tolerance analysis was performed by calculating the root-mean-squared (rms) wavefront error, i.e., deviations from an ideal spherical wavefront. The nominal error of the lens design is 0.007. Monte Carlo simulations were performed with 5000 runs; more than 90% of the trials had a rms wave front error less than 0.05, which is below the accepted practical limit (0.07) for a diffraction-limited optical system.

The dichroic coatings on elements 2 and 3 that enable zoom operation lead to non-reciprocal propagation of the excitation and the emitted light. Therefore, epi-collection of the two-photon excited signal through the delivery fiber is inefficient. 10 flexible, plastic optical fibers (POFs) with large core diameter (500 um) were used located just behind element 2 to collect the emitted light signal.

All references, including publications, patent applications, and patents cited herein are hereby incorporated by reference in their entireties to the extent allowed, and as if each reference was individually and specifically indicated to be incorporated by reference and was set forth in its entirety herein.

The use of the terms "a" and "an" and "the" and similar referents in the context of describing the invention (especially in the context of the following claims) is to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening.

The recitation of ranges of values herein is merely intended to serve as a shorthand method of referring individually to each separate value falling within the range, unless otherwise indicated herein, and each separate value is incorporated into the specification as if it was individually recited herein.

All methods described herein may be performed in any suitable order unless otherwise indicated herein or otherwise clearly contradicted by context. The use of any and all examples, or exemplary language (e.g., "such as") provided herein, is intended merely to better illuminate embodiments of the invention and does not impose a limitation on the scope of the invention unless otherwise claimed.

No language in the specification should be construed as indicating any non-claimed element as essential to the practice of the invention.

It will be apparent to those skilled in the art that various modifications and variations can be made to the present invention without departing from the spirit and scope of the invention. There is no intention to limit the invention to the specific form or forms disclosed, but on the contrary, the intention is to cover all modifications, alternative constructions, and equivalents falling within the spirit and scope of the invention, as defined in the appended claims. Thus, it is intended that the present invention cover the modifications and variations of this invention provided they come within the scope of the appended claims and their equivalents.

What is claimed is:

1. A microendoscope comprising:
    a tube housing that defines an optical path;
    a lens assembly positioned within a distal end of the tube housing, wherein the distal end of the tube housing is shaped to provide an increase in the collection of light emission from a sample, and wherein the lens assembly comprises within the optical path:
        a second element including a convex proximal surface and a concave distal surface; and
        a third element including a convex proximal surface mated with the concave distal surface of the second element, as well as a straight distal surface, at least a portion of each of the second element and the third element comprising a dichroic coating; and
    a plurality of light pipes directly coupled to a proximal side of the lens assembly;
    wherein an interior finish of a region of the distal end of the tube housing comprises a reflective material coating for emission wavelengths, and wherein at least the region of the distal end of the tube housing has a parabolic or spherical shape configured to concentrate a light emission into a ring area, and wherein the light pipes are positioned within the ring area.

2. The microendoscope of claim 1, wherein the lens assembly provides the microendoscope with a tunable magnification factor as a function of irradiation wavelength.

3. The microendoscope of claim 1, wherein the lens assembly comprises a fixed, catadioptric zoom lens.

4. The microendoscope of claim 1, wherein the dichroic coating is configured to provide optical zoom capability.

5. The microendoscope of claim 4, wherein the dichroic coating is deposited at a central part of a proximal surface of a first lens and at a peripheral region of a proximal surface of a second lens.

6. The microendoscope of claim 4, wherein the lens assembly is capable of a dual modality or a dual optical zoom.

7. The microendoscope of claim 6, wherein the dual optical zoom is achieved by changing the wavelength of an excitation light.

8. The microendoscope of claim 1, further comprising a first element separated along an optical path from the convex proximal surface of the second element.

9. The microendoscope of claim 1, wherein the lens assembly is configured to utilize a first illumination wavelength for a reflectance microscopy magnification, and further configured to utilize a second illumination wavelength for a fluorescence microscopy magnification.

10. The microendoscope of claim 1, wherein the lens assembly does not comprise any mechanical adjustment.

11. The microendoscope of claim 1, wherein the light pipes are configured to collect at least 40% of a light emission.

12. The microendoscope of claim 1, wherein the microendoscope is configured to collect at least 40% of a light emission.

13. A microendoscopy method comprising:
    providing a microendoscope comprising: (i) a tube housing that defines an optical path; and (ii) a lens assembly positioned within a distal end of the tube housing, wherein the distal end of the tube housing is shaped to facilitate optimized collection of light emission from the sample when examined using the microendoscope, and further wherein the lens assembly comprises within the optical path: a second element including a convex proximal surface and a concave distal surface, and a third element including a convex proximal surface mated with the concave distal surface of the second element, as well as a straight distal surface, at least a portion of each of the second element and the third element including a dichroic coating; and (iii) a plurality of light pipes directly coupled to a proximal side of the lens assembly; wherein an interior finish of a region of the distal end of the tube housing comprises a reflective material coating for emission wavelengths, and wherein at least the region of the distal end of the tube housing has a parabolic or spherical shape configured to concentrate a light emission into a ring area, and wherein the light pipes are positioned within the ring area; and
    examining the sample while using the microendoscope.

14. The microendoscopy method of claim 13, wherein the lens assembly provides for a tunable magnification factor as a function of irradiation wavelength.

15. The microendoscopy method of claim 13, wherein the lens assembly comprises a fixed, catadioptric zoom lens assembly.

* * * * *